United States Patent [19]

Dazzi et al.

[11] 3,935,251

[45] Jan. 27, 1976

[54] 2,4,8-TRICHLORO-TRI AND TETRA BROMODIBENZOFURANS

[75] Inventors: Joachim Dazzi, Riehen; Rudolf Kirchmayr, Munchenstein; Henri Dietrich, Arlesheim, all of Switzerland

[73] Assignee: Ciba-Geigy Corporation, Ardsley, N.Y.

[22] Filed: Mar. 7, 1974

[21] Appl. No.: 449,176

[30] Foreign Application Priority Data

Mar. 20, 1973  Switzerland.......................... 4028/73

[52] U.S. Cl. ....... 260/346.2 M; 252/8.1; 106/15 FP
[51] Int. Cl.$^2$....................................... C07D 307/91
[58] Field of Search ............................. 260/346.2 M

[56] References Cited
UNITED STATES PATENTS 2,076,430   4/1937   Hanson et al. .............. 260/346.2 M
3,201,418   8/1965   McCall et al. ................ 260/346.2 M

OTHER PUBLICATIONS

Plimmer et al., J. Agr. Food Chem., Vol. 21, No. 1, 1973, p. 90–93.

Primary Examiner—John M. Ford
Assistant Examiner—Bernard I. Dentz
Attorney, Agent, or Firm—Nestor W. Shust

[57] ABSTRACT

Polyhalogenated dibenzofuranes having at least six halogen atoms are prepared by halogenation of 2,4,8-trichlorodibenzofurane or of dibenzofurane. The halogenation may be achieved by $Cl_2$, $Br_2$, $SO_2Cl_2$, $S_2Cl_2$ or similar halogen donors. The products are flameproofing agents for polymers, especially for polyesters and polyolefins. Examples are octachloro-, trichlorotribromo- and trichlorotetrabromo-benzofurane.

2 Claims, No Drawings

2,4,8-TRICHLORO-TRI AND TETRA BROMODIBENZOFURANS

The present invention relates to new polyhalogenated dibenzofuranes, a process for their manufacture, their use as flameproofing agents for synthetic organic polymers and flameresistant compositions of synthetic organic polymers and the new polyhalogenated dibenzofuranes.

Most synthetic organic polymers are inflammable, which restricts their use to certain fields. The result of this is that in cases where an ignition hazard is to be expected, either polymers which are inherently of low inflammability are used, or so-called flameproofing agents are added to the inflammable polymers.

Organic halogen compounds are extensively used as flameproofing agents, and frequently antimony trioxide is also added as a synergistic agent. Known examples thereof are chlorinated paraffins, halogenated trialkyl phosphates or polybrominated aromatic compounds.

Many of these known flameproofing agents are adequately compatible only with certain polymers whilst they do not mix with other polymers, or tend to sweat out. Some halogenated flameproofing agents possess only moderate heat stability so that when admixed to a hot polymer melt they partially decompose at this stage and cause discolourations. Other halogenated flameproofing agents display a relatively high volatility. They tend to sublime at elevated temperature and hence make incorporation into polymers, and thermal moulding of the polymers equipped with such flameproofing agents, more difficult. Yet other flameproofing agents lower the softening point and impair the mechanical or thermo-mechanical properties of the polymers.

It has now been found that polyhalogenated dibenzofuranes of the formula

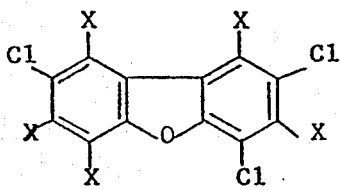
(I)

in which the individual substituents X independently of one another denote hydrogen, chlorine or bromine, and at least three substituents X denote chlorine or bromine, possess an excellent flameproofing action for synthetic organic polymers without suffering from the abovementioned disadvantages.

Compounds which have proved particularly effective are octachlorodibenzofurane of the formula

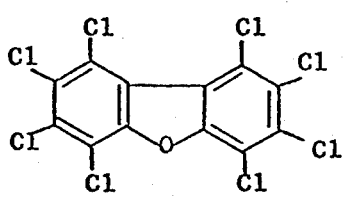

as well as 2,4,8-trichloro-tetrabromodibenzofuranes of the formula

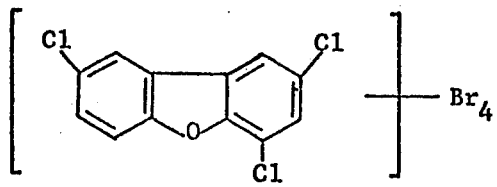

and 2,4,8-trichloro-tribromodibenzofuranes of the formula

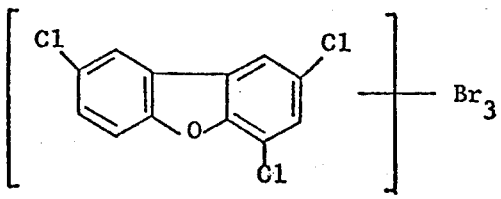

The new polyhalogenated dibenzofuranes of the formula I can be manufactured according to methods which are in themselves known, in particular by either (a) reacting debenzofurane with chlorine or a chlorine donor and optionally subsequently with bromine or a bromine donor or (b) by reacting 2,4,8-trichlorodibenzofurane with chlorine or a chlorine donor and/or with bromine or with a bromine donor in the presence of one or more catalysts.

Preferably 2,4,8-trichlorodibenzofurane is used as the starting material. The two starting materials mentioned are known and technically readily accessible compounds.

The halogenation can be effected either with elementary chlorine or bromine or with known chlorine or bromine donors. As the latter it is possible to use, for example, sulphuryl chloride, sulphur monochloride, N-bromosuccinimide or a dioxane-bromine complex and also mixtures of such componds, such as, for example, mixtures of sulphuryl chloride and sulphur monochloride.

The halogenating agent must be employed in at least stoichiometric amounts; preferably, the halogenating agent is used in a slight excess over the stoichiometrically required amount.

If chlorine donors or bromine donors of the type mentioned are used for the halogenation, they can be used in a larger excess, and then simultaneously also serve as the solvent. The use of a solvent is advisable when halogenating with elementary chlorine or bromine. Suitable solvents for this purpose are above all halogenated hydrocarbons such as, for example, chloroform, tetrachloromethane, tetrachloroethane or 1,2-dibromoethane. Concentrated sulphuric acid or oleum or chlorosulphonic acid are also suitable for this purpose.

As catalysts, it is possible to use the compounds generally employed for the nuclear halogenation of aromatic hydrocarbons, such as iron, especially iron filings, iron-III chloride, aluminium bromide, aluminium chloride or iodine.

In general, the halogenation is carried out at temperatures between 20° and 120°C, especially 50° and 90°C.

The polyhalogenated dibenzofuranes according to the invention can be isolated from the reaction mixture according to customary processes, for example by filtration or by distilling off the solvent. If it is desired to purify the products, this can be done by recrystallisation.

The polyhalogenated dibenzofuranes according to the invention are colourless crystalline substances which are insoluble in an aqueous medium. Their solubility in organic solvents is also low at room temperature.

The polyhalogenated dibenzofuranes according to the invention, of the formula I, can be used as flameproofing agents for synthetic organic polymers. They are distinguished by a good to very good flameproofing action, coupled with high heat stability, low volatility and good compatibility. The present invention therefore also relates to the use of polyhalogenated dibenzofuranes of the formula I as flameproofing agents for synthetic organic polymers. It relates, furthermore, to flame-repellent compositions of synthetic organic polymers which contain at least one polyhalogenated dibenzofurane, according to the invention, as the active compound. The synthetic organic polymers can be polymers, polycondensates or polyadducts. They can be linear polymers with thermoplastic properties, or three-dimensionally crosslinked thermosetting resins. Finally, the term synthetic organic polymers also embraces the pre-products of such polymers, so-called prepolymers. Examples of such polymers are: polymers or copolymers of olefines, including those of styrene, or acrylic and methacrylic acid esters, of acrylonitrile, of vinyl acetate, of vinyl chloride and of unsaturated polyesters, and also epoxy resins, phenolic resins, linear polyesters and polyamides.

The use of the materials according to the invention as flameproofing agents for linear aromatic polyesters, such as polyethylene terephthalate or polybutylene terephthalate, for linear polyamides, such as nylon 6 or nylon 66, for polyolefines, such as polyethylene or polypropylene, for epoxy resins and for unsaturated polyester resins is of particular interest.

The flame-retardant polyhalogenated dibenzofuranes of the formula I can be admixed with, or worked into, the synthetic organic polymers at any desired stage of manufacture or processing, according to methods which are in themselves known. Thus, for example, they can be added to the corresponding monmers monomers polymerisation or, preferably, to the previously formed polymers before or optionally also during their processing.

In the case of solutions of polymers or in the case of liquid or pasty polymers or prepolymers, the admixing can be effected by a stirrer or kneader, whilst in the case of elastic soft polymers it can be effected on a mixing mill. Thermoplastics are mostly mixed in the molten form with the flameproofing agent and this can be effected, for example, in an extruder. In the latter process, the low volatility of the halogenodibenzofuranes according to the invention is of particular advantage.

The dibenzofuranes according to the invention can be added to the polymers in any desired form; however, they are preferably used in the form of fine powders such as are obtained by customary methods of comminution, especially by grinding.

The content of flame-retardant dibenzofuranes of the formula I in the polymers can vary within wide limits depending on the inflammability and/or use of the polymers. In general, it is advisable to add 1–40, preferably 5–20, percent by weight of the dibenzofurane, relative to the polymer The flame-retardant action of the halogenodibenzofuranes according to the invention can be boosted by the addition of antimony trioxide. Advantageously, the antimony trioxide is used in such ratio to the polyhalogenated dibenzofurane that the weight ratio of antimony to halogen is 1:1 to 1:5, with a ratio of about 1:3 showing a particularly strong synergistic action.

Further conventional additives such as fillers, glass fibres, pigments, plasticisers, blowing agents, stabilisers, light protection agents and antioxidants can also be co-used. The flame-resistant compositions according to the invention can be converted in a known manner into mouldings, profiles, fibres, films, foams, laminates or coatings. The fibres obtained therefrom are of particular interest since the flameproofing of textiles is an important problem.

The examples which follow serve to explain the invention further. Unless stated otherwise, the precentages mentioned are percentages by weight.

EXAMPLE 1

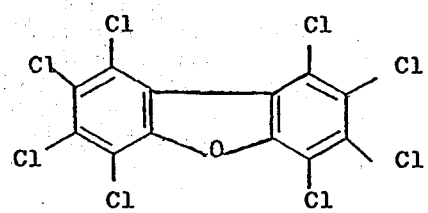

Manufacture of octachlorodibenzofurane a. in organic solvents 100 g of 2,4,8-trichlorodibenzofurane, 10 g of sulphur monochloride and 500 g of sulphuryl chloride are warmed to 60°C. A solution of 10 g of aluminium chloride in 300 ml of sulphuryl chloride is added dropwise at this temperature over the course of 40 minutes. The light yellow reaction mixture turns dark, with vigorous evolution of gas, complete solution being achieved temporarily. Towards the end of the dropwise addition, a crystalline precipitate begins to separate out. After the dropwise addition, the reaction mixture is stirred for a further hour at 60°C and excess sulphuryl chloride is then distilled off under normal pressure. The residue is taken up in 1,000 ml of hot carbon tetrachloride and the resulting suspension is briefly brought to the reflux temperature and then cooled. The crystalline precipitate is filtered off, washed with a little chloroform and dried. The octachlorodibenzofurane of the above formula is thus obtained in the form of white crystals of melting point 258°–260°C.

Yield: 90% of theory, based on 2,4,8-trichlorodibenzofurane employed.

Analysis for $C_{12}Cl_8O$ (molecular weight = 443.75)

| | | |
|---|---|---|
| calculated: | C 32.48% | Cl 63.94% |
| found: | C 32.77% | Cl 63.87% |

If the chlorination of 2,4,8-trichlorodibenzofurane is carried out in tetrachloroethane by means of chlorine in the presence of catalytic amounts of iron filings, octachlorodibenzofurane is again obtained.

The same compound is obtained when chlorinating dibenzofurane with chlorine in the presence of iron filings or with sulphuryl chloride in the presence of aluminium chloride and sulphur monochloride as catalysts.

b. in inorganic solvents 136.5 g of 2,4,8-trichlorodibenzofurane are carefully introduced into 1,400 g of chlorosulphonic acid at 15°C, the mixture is slowly heated to 60°C, 1 g of iodine is added and chlorine is passed in. The course of the reaction can be followed by pouring a sample of the reaction mixture onto ice, stirring in a mixer and filtering. The course of the reaction, and the purity of the end product, are determined from the Cl content found and from the melting point. The better is the distribution of chlorine and the stirring of the reaction mixture, the more rapidly and completely does the chlorination take place. The reaction time is 7–11 hours. Temperature 60°–80°C. After the chlorination, nitrogen is passed through the reaction mixture which is then poured onto ice. The precipitate is filtered off, washed until neutral and dried. Octachlorodibenzofurane is thus obtained in the form of white crystals of melting point 262°–263°C.

Yield: 88% of theory, based on 2,4,8-trichlorodibenzofurane employed.

Analysis for $C_{12}Cl_8O$ (molecular weight = 443.75):

| | | |
|---|---|---|
| calculated: | C 32.48% | Cl 63.94% |
| found: | C 32.88% | Cl 63.35%. |

If the chlorination of 2,4,8-trichlorodibenzofurane is carried out in 100% strength sulphuric acid with chlorine in the presence of catalytic amounts of iron filings, octachlorodibenzofurane is again obtained.

The same compound is obtained on chlorinating 2,4,8-trichlorodibenzofurane with chlorine in the presence of catalytic amounts of iodine in oleum containing 30–60% of $SO_3$.

EXAMPLE 2

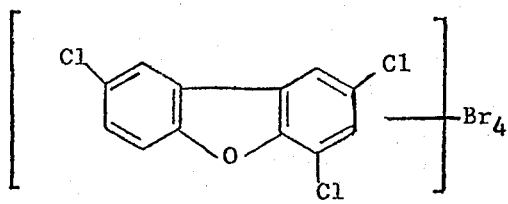

Manufacture of
2,4,8-trichloro-tetrabromodibenzofurane a. in organic solvents 108 g of 2,4,8-trichlorodibenzofurane and 1 g of iron filings are suspended in 600 ml of 1,2-dibromoethane. 320 g of bromine are added dropwise to this suspension over the course of 3 hours whilst stirring and gradually warming the mixture to 80°C. In the course thereof, a red-brown solution is obtained temporarily, with vigorous evolution of gas, and after about half the amount of bromine has been added a crystalline precipitate forms. After completion of the addition of bromine, the mixture is warmed to 80°–100°C for a further hour and is then cooled to room temperature. 150 ml of 1-pentene are added dropwise to the reaction mixture whilst cooling. This decolourises the reaction mixture. The crystalline precipitate is filtered off, washed with a little chloroform and dried. This gives 2,4,8-trichloro-tetrabromodibenzofurane of the above formula in the form of white crystals of melting point 289°–290°C.

Yield: 81% of theory, based on 2,4,8trichlorodibenzofurane employed.

Analysis for $C_{12}HCl_3Br_4O$ (molecular weight 587.19)

| | | | |
|---|---|---|---|
| calculated: | C 24.55% | Cl 18.11% | Br 54.44% |
| found: | C 24.34% | Cl 17.61% | Br 54.87%. |

If the bromination of 2,4,8-trichlorodibenzofurane is carried out in tetrachloroethane as the solvent and the same procedure as that described above is followed, 2,4,8-trichlorotetrabromodibenzofurane is again obtained.

b. in inorganic solvents 108 g (0.4 mol) of 2,4,8-trichlorodibenzofurane and 1 g of iron filings are suspended in 1,300 g of oleum (30% $SO_3$ content). 320 g (2 mols) of bromine are added dropwise to this suspension over the course of 4.5 hours with rapid stirring and whilst gradually heating to 90°C. The end product separates out as a crystalline precipitate during the addition of bromine. After completion of the addition of bromine, the mixture is warmed to 90°–100°C for a further hour and cooled to room temperature. Excess bromine is removed by addition of sodium sulphite ($Na_2SO_3 \cdot 7H_2O$) until the reaction mixture has been decolourised. The reaction mixture is poured onto ice; the crystalline precipitate is filtered off, washed until neutral, filtered off, washed with a little methanol and dried. 2,4,8-Trichloro-tetrabromodibenzofurane is thus obtained in the form of white crystals of melting point 288°–290°C.

The yield is 77% of theory, relative to 2,4,8-trichlorodibenzofurane employed.

Analysis for $C_{12}HCl_3Br_4O$ (molecular weight 587.19)

| | | | |
|---|---|---|---|
| calculated: | C 24.55% | Cl 18.11% | Br 54.44% |
| found: | C 24.31% | Cl 18,31% | Br 54.08%. |

IF the bromination of 2,4,8-trichlorodibenzofurane is carried out in 100% strength sulphuric acid with bromine in the presence of catalytic amounts of iron filings, 2,4,8-trichloro-tetrabromodibenzofurane is again obtained.

The same compound is obtained on bromination of 2,4,8-trichlorodibenzofurane with bromine in the presence of catalytic amounts of iron filings in chlorosulphonic acid.

EXAMPLE 3

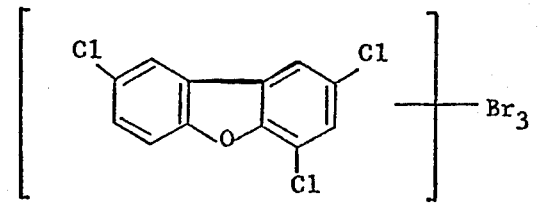

Manufacture of 2,4,8-trichloro-tribromodibenzofurane

The procedure of Example 2 is followed, using 1,2-dibromoethane as the solvent, but 3 equivalents of bromine are used to brominate 2,4,8-trichlorodibenzofurane. 2,4,8-Trichloro-tribromodibenzofurane is obtained in the form of white crystals of melting point 220°–222°C.

Analysis for $C_{12}H_2Cl_3Br_3O$ (molecular weight 508.2)

| | | | | |
|---|---|---|---|---|
| calculated: | C 28.3% | H 0.4% | Cl 20.8% | Br 47.1% |
| found: | C 27.9% | H 0.3% | Cl 20.8% | Br 47.6% |

EXAMPLE 4

Commercially available granules of polyethylene terephthalate are mixed with the flameproofing agent and with antimony trioxide, both in a finely pulverulent form, in the concentrations shown below. The mixture is agitated for 1 hour in a tumbler barrel and then fused for 35 minutes at 290°C under nitrogen in a glass tube. The melt is cooled to room temperature. Filings are drilled from the regulus thus obtained and are pressed together with glass fibre marquisette in a hydraulic laboratory press at 280°C for 6 minutes to give sheets 0.3 mm thick. The inflammability of these samples is determined by the LOI method described by C. P. Fenimore and J. F. Martin in Combustion and Flame 10, No. 2, 135–139 (June 1966). In this method, the sample is ignited in an atmosphere of nitrogen and oxygen of varying composition by volume, and the composition by volume at which combustion of the sample can just be maintained is determined. The LOI index is the minimum concentration in a nitrogen oxygen mixture at which the test specimen just continues to burn. The higher is the LOI, the lower is the inflammability, that is to say the more effective is the flameproofing additive.

The results thus obtained are summarised in the table which follows.

| Flameproofing agent | Amount of flameproofing agent* | Amount of $Sb_2O_3$* | Appearance of sheet | LOI (Limiting Oxygen Index) |
|---|---|---|---|---|
| Octachlorodibenzo-furane (Example 1) | 7.8% | 2% | white | 0.265 |
| Trichloro-tetrabromo-dibenzofurane (Example 2) | 9.1% | 1.2% | white | 0.291 |
| Polyester without flameproofing agent | — | — | clear | 0.201 |

*% by weight relative to polyethylene terephthalate

EXAMPLE 5

Portions of 100 parts by weight of a liquid unmodified epoxy resin prepolymer having an epoxide content of 5.25 equivalents/kg and a viscosity of 10,000 cP at 25°C, of which the main constituent consists of the diglycidyl ether of 4,4,'-dihydroxy-2,2-diphenylpropane, were mixed with 1 part by weight of a commercially available highly disperse silica and various amounts of flameproofing agents by manual stirring and then ground on a triple roll mill to give an intimate mixture. These mixtures were warmed to 80°C and 26 parts by weight of 4,4'-diaminodiphenylmethane were added, as the curing agent, at this temperature. As soon as this compound had dissolved, the air which had been stirred in was removed by applying a vacuum and the mixture was cast into aluminium moulds, prewarmed to 80°C in order to produce bar-shaped test specimens of dimensions 120 × 15 × 10 mm, and cured for 2 hours at 80°C and subsequently for 8 hours at 140° C.

These test specimens were used for determination of the Martens heat distortion point according to DIN 53,458 and of the inflammability according to the following test method:

The horizontally clamped test bar is exposed to the flame of a gas burner for 1 minute. The flame height of the vertical burner is 10 cm.

The burner is inclined at 45° and the test bar is placed in the flame so that the lower 15 mm broad surface of the bar is 3 cm above the upper edge of the burner and its end face is at a horizontal distance of 1 cm from the lower edge of the burner. The burning time from removal of the flame to cessation of burning is assessed. The results of the tests are listed in the table which follows:

| Flameproofing agent used | Amount added* | Halogen content of the mixture, in % by weight | Martens temperature (DIN 53,458) | Burning time in seconds |
|---|---|---|---|---|
| Octachlorodibenzo-furane (Example 1) | 3 | 1.47 | 141°C | 14 |
|  | 5 | 2.42 | 140°C | 5 |
|  | 10 |  | 142°C | 4 |
| Trichloro-tetrabromo-dibenzofurane (Example 2) | 3 | 1.68 | 141°C | 60 |
|  | 5 | 2.75 | 142°C | 9 |
|  | 10 | 5.31 | 144°C | 4 |
| Comparison without flameproofing agent | — | — | 142°C | >60 |

*Parts by weight per 100 parts by weight of epoxy resin, 26 parts by weight of diamine curing agent and 1 part by weight of high disperse silica.

It can be seen from the table that the additives according to the invention do not cause any lowering of the heat distortion point which, as is known, is an important technical property when using epoxy resins. The addition of 3 or 5% of the dibenzofuranes, relative to the epoxy prepolymer, suffices to achieve satisfactory flameproofing with a burning time of less than 15 seconds. The economy of the process can be appreciated, above all, from the relation of halogen content to flameproofing action.

EXAMPLE 6

Polypropylene granules of melt index 3.2 g/10 minutes/230°C, containing 0.2% of a stabiliser consisting substantially of octadecyl-3-(3,5-di-tert.-butyl-4-hydroxyphenyl)-propionate, was mixed with the flameproofing agents described in Example 1 and 2 and with antimony trioxide, in the concentrations shown below, on a two-roll mill at 180°C for 10 minutes. Sheets 0.3 mm thick were pressed from the mill hide together with glass fibre marquisette for 6 minutes at 245°C. The LOI values for these sheets were determined as described in Example 4. The results are summarised in the table which follows.

| Flameproofing agent | Amount of flameproofing agent*) | Amount of Sb$_2$O$_3$*) | Appearance of sheet | LOI |
|---|---|---|---|---|
| Octachlorodibenzofurane (Example 1) | 7.8% | 2% | white | 0.194 |
| Trichloro-tetrabromodibenzofurane (Example 2) | 9.1% | 2% | white | 0.208 |
| None (comparison) | — | — | white | 0.181 |

*)% by weight based on polypropylene

We claim:

1. A 2,4,8-Trichloro-tetrabromodibenzofuran of the formula

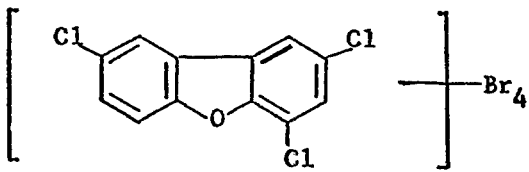

2. A 2,4,8-Trichloro-tribromodibenzofuran of the formula

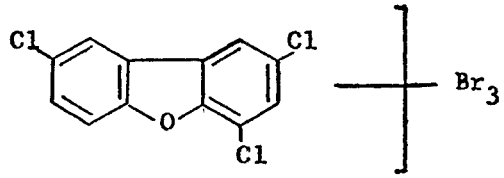

* * * * *